United States Patent
Prasad et al.

(10) Patent No.: US 9,655,966 B2
(45) Date of Patent: *May 23, 2017

(54) MICRONUTRIENT FORMULATIONS FOR RADIATION APPLICATIONS

(76) Inventors: Kedar N. Prasad, San Rafael, CA (US); Gerald M. Haase, Greenwood Village, CO (US); William C. Cole, Novato, CA (US)

( * ) Notice: Subject to any disclaimer, the term of this patent is extended or adjusted under 35 U.S.C. 154(b) by 836 days.

This patent is subject to a terminal disclaimer.

(21) Appl. No.: 12/284,841

(22) Filed: Sep. 25, 2008

(65) Prior Publication Data

US 2011/0172179 A1    Jul. 14, 2011

Related U.S. Application Data

(63) Continuation-in-part of application No. 10/229,274, filed on Aug. 28, 2002, now Pat. No. 7,449,451.

(51) Int. Cl.
| | |
|---|---|
| A61K 45/06 | (2006.01) |
| A61K 31/015 | (2006.01) |
| A61K 31/714 | (2006.01) |
| A61K 31/59 | (2006.01) |
| A61K 31/555 | (2006.01) |
| A61K 31/525 | (2006.01) |
| A61K 31/4184 | (2006.01) |
| A61K 31/51 | (2006.01) |

(52) U.S. Cl.
CPC ............ *A61K 45/06* (2013.01); *A61K 31/015* (2013.01); *A61K 31/4184* (2013.01); *A61K 31/51* (2013.01); *A61K 31/525* (2013.01); *A61K 31/555* (2013.01); *A61K 31/59* (2013.01); *A61K 31/714* (2013.01); *A23V 2002/00* (2013.01)

(58) Field of Classification Search
CPC .......... A23V 2002/00; A23V 2250/211; A23V 2250/708; A23V 2200/02; A23V 2250/026; A23V 2250/0616; A23V 2250/712; A23V 2250/1578; A23V 2250/1586; A23V 2250/1626; A23V 2250/1642; A23V 2250/702; A23V 2250/704; A23V 2250/7106; A61K 2300/00; A61K 31/015; A61K 31/4184; A61K 31/51; A61K 31/525; A61K 31/555; A61K 31/59; A61K 31/714; A61K 45/06

USPC .......................................................... 514/52

See application file for complete search history.

(56) References Cited

U.S. PATENT DOCUMENTS

| | | | | |
|---|---|---|---|---|
| 3,860,733 | A | * 1/1975 | Morse et al. .................. | 426/302 |
| 6,143,301 | A | * 11/2000 | de la Harpe et al. ......... | 424/770 |
| 2003/0064955 | A1 | * 4/2003 | Prasad et al. .................... | 514/52 |

FOREIGN PATENT DOCUMENTS

| | | | |
|---|---|---|---|
| EP | 1163904 | * 12/2001 | ........... A61K 31/195 |
| EP | 1733720 | * 12/2006 | ............. A61K 31/01 |

* cited by examiner

*Primary Examiner* — Rachael Bredefeld
(74) *Attorney, Agent, or Firm* — Dan M. De La Rosa

(57) ABSTRACT

A radioactive protection micronutrient formulation system is provided and the system comprises: a formulation consisting essentially of antioxidants, the antioxidants are selected from the group consisting essentially of vitamin C, vitamin E, N-acetyl cysteine, natural mixed carotenoids, and alpha-lipoic acid, vitamin A (palmitate), vitamin D-3 (cholecalciferol), thiamine mononitrate, riboflavin, niacinamide ascorbate, d-calcium pantothenate, pyridoxine hydrochloride, cyanocobalamin, folic acid, D-Biotin, selenium (1-selenomethionine), chromium picolinate, zinc glycinate, calcium citrate and magnesium citrate and mixtures thereof; and plus a booster formulation selected from a group consisting essentially of vitamin C, d-alpha tocopheryl acid succinate, alpha tocopherol, N-acetyl cysteine, natural mixed carotenoids and alpha lipoic acid, the formulation is designed to reduce the risk in humans exposed to doses of ionizing radiation of becoming subjected to at least one condition selected from the group consisting essentially of radiation-induced acute leukemia, breast cancer, thyroid cancer and other somatic and heritable mutations.

11 Claims, No Drawings

MICRONUTRIENT FORMULATIONS FOR RADIATION APPLICATIONS

RELATED APPLICATION

This application is a continuation-in part application of U.S. application Ser. No. 10/229,274, entitled "Use of Multiple Antioxidant Micronutrients as Systemic Biological Radioprotective Agents" which was filed on Aug. 28, 2002 now U.S. Pat. No. 7,449,451 and has now been granted a Notice of Allowance and is related to U.S. Provisional Application No. 60/315,522, filed Aug. 29, 2001, entitled "Use of Multiple Antioxidant Micronutrients as Systemic Biological Radioprotective Agents".

BACKGROUND OF THE INVENTION

Field of the Invention

This invention relates to a use of micronutrient formulations to reduce the effects of radiation on humans.

Description of the Related Art

Ionizing radiation (X-rays and gamma rays) has proven to be a double-edged sword in clinical Medicine since its discovery by Dr. Wilhelm Roentgen in 1895 (1,2). Energy wavelength progresses along the electromagnetic continuum from longer ranges (radiowaves, microwaves, infrared, and heat waves) to medium wavelengths (visible light, ultraviolet light) to shorter wave lengths (ionizing radiation, e.g., x-rays and gamma rays). It is these x-rays and gamma rays that are able to drive electrons out of their normal atomic orbits with enough kinetic energy to generate charged molecules (including free radicals) that damage cells. In addition to the initial realization by the medical community that ionizing radiation could detect as well as treat human diseases, came the unfortunate demonstration that it could also induce serious illness.

In fact, most of the ionizing radiation to which the human population is exposed, other than that received from environmental sources, is from the diagnostic and screening imaging machines employed by today's clinical healthcare professionals. For example, in the past, x-ray-induced skin cancers were noted with higher frequency in radiologists. Obviously, whenever x-rays are employed, it is done with caution so that patients and healthcare providers are exposed to as low a does as possible. Physicists and nuclear engineers have devised improved equipment and radiation beam delivery systems to reduce the level of diagnostic radiation dose without compromising the quality of images. However radiation biologists agree that there is no threshold dose below which there is no risk of cellular damage. In fact, even a single radiation track that crosses a cellular nucleus has a very low, but finite, probability of generating damage that may result in cellular dysfunction, somatic and heritable mutations, and subsequent genetic implications.

While most clinical radiologists believe the risks of x-ray exposure are very small, residual biologic effects from alteration in structure are dependent on whether the cell repairs its injured components. Although the vast majority of damage is repaired, some may be unrepaired or misrepaired and there in lies the problem. In adults, most radiation researchers consider cancer induction to be the most important somatic effect of low dose ionizing radiation and this outcome may occur in nearly all the tissues of the human body. Academic radiologists are also raising future disease concerns regarding pediatric age groups because of the increased numbers of imaging studies now being performed in younger populations (3). In light of these concepts the healthcare profession states that ionizing radiation exposure should only occur when there is a defined healthcare benefit, or indicated when the risk-benefit ratio is favorable to the patient. The critical concept has been always to protect humans by physical local factors, such as shielding and decreasing doses and x-rays times. However, no one has previously considered the additional aspects to a strategy of systemic biological protection.

Recent advances in imaging technology have made possible the detection of many illnesses such as heart disease, cancer, neurologic diseases, arthritis and other acute or chronic conditions. It is also significant development that this technology may detect the problem at an early stage when treatment interventions allow for less invasive therapeutic procedures and/or surgical operations and yet achieve improved health outcomes. In this environment, the number of diagnostic x-rays performed is truly enormous. It was estimated in the United States for the period 1985 to 1990 at least 800 diagnostic studies per 1,000 population were performed and this excluded dental x-rays and nuclear medicine (4). The importance of these finding can be appreciated since it is probable that frequent low dose radiation exposures may be more damaging than a single higher dose exposure on the criteria of gene mutations and cancer promotion.

The current era has seen an explosion of diagnostic imaging equipment including the introduction of computed tomography, digital radiography, expanded nuclear medicine applications, interventional radiology, and lengthening fluoroscopic procedures. In concert with these technical innovations, the concept of early disease detection and screening large populations to employ illness prevention strategies will generate further rapid expansion of members of imaging studies with increased ionizing radiation exposure to the public. As a direct consequence of this new proactive healthcare approach, imaging will be performed in many more, otherwise healthy, people and asymptomatic "at risk" populations. In addition, initial exposures will occur at an earlier age and the mandate of serial follow-up imaging will result in an overall greater frequency of x-ray studies.

The doses of ionizing radiation exposure in imaging studies vary dramatically from less than 0.1 rem (1 millisievert, mSv, for x-rays and gamma rays, 1 rem=1 rad) per test for some procedures to others that involve levels in some organs in excess of 10 rem per test. Table 1 lists a sampling of common studies (5-8). Note that while the red marrow dose is usually the reported "standard", the actual target organ dose is actually often significantly higher. For example, mammography exposes the actual breast tissue to approximately 700 mrem, virtually equal to the total skin entrance dose. Likewise, thallium scanning exposes the thorax to approximately 1000 mrem, about 20 times the red marrow dose.

TABLE 1

| Procedure | Effective Dose Equivalent (HE) | | Skin Entrance Dose |
|---|---|---|---|
| | mSv* | mrem | mrem |
| Diagnostic X-ray | | | |
| Chest AP, 100 kVp | 0.015 | 1.5 | 10 |
| Lumbar spine AP, 80 kVp | 0.273 | 27.3 | 359 |
| Upper G.I. | 4.1 | 410 | 2300/min |

TABLE 1-continued

| | | | |
|---|---|---|---|
| Coronary angioplasty | 50-150/min | 5000-15000/min | 25000/min |
| Head CT | 0.8-5 | 80-500 | 4500 |
| Abdomen CT | 6-24 | 600-2400 | 2000 |
| Dental | 0.01 | 1 | 350 |
| Electron beam CT heart | 0.14-0.3 | 14-30 | 150 |
| Mammogram | ** | ** | 700 |
| | mSv | mrem | mrem |
| Nuclear medicine | | | |
| 18F-Fluorodeoxyglucose, 10 mCi | 9.99 | 999 | NA |
| 99 mTc-MAA Lung Scan (perfusion only) 5 mCI | 2.03 | 203 | NA |
| 99 mTc-HDP Bone scan 20 mCi | 5.92 | 592 | NA |
| 201 TI Thallium scan 3 mCi | 25.53 | 2553 | NA |

*Seivert is the official unit of biological radiation dose.
One Sv = 100 rem.
ND = Data not available
** = Dose negligible
NA = Not Applicable Depending on the age of the individual, frequency of testing, exposure time, and total dose, the diagnostic or screening imaging studies could increase the risk of somatic damage (some forms of cancer such as leukemia, breast, and thyroid) as well as genetic damage (such as with gonadal exposure) in the target population. In fact, radiation experts are beginning to call for special attention to issues of exposure from CT Scanning in young patients (9). It should be emphasized that the risk of radiation injury produced by diagnostic doses below 0.5 rem is very small in comparison to other agents that are present in the diet of the natural environment. However, regardless of the "insignificant" risk with any individual exposure or imaging event, the total effects of ionizing radiation are on-going, cumulative over time, have the potential for lifelong expression, and may have a future generational genetic impact.

It should be anticipated that as more sophisticated imaging studies are available for diagnosis and screening, the individual small risks may add up over a lifetime. For example, nuclear medicine has been expanded to new techniques which include intravenous systemic injection of radionuclides and expose various body organs to differing radiation doses (10). The recent impact of interventional techniques often combined with surgical procedures also increases the imaging risks. Furthermore, advance fluoroscopic imaging used for technical procedures such as percutaneous transluminal angioplasty, transhepatic cholangiography, stent and drainage placements as well as venous access procedures may involve significant radiation exposure (11). In fact by the year 2000 in the United States alone, about 750,000 patients underwent coronary balloon angioplasty (12). Finally, the most recent technical innovations utilized in screening procedures, such as spiral and electron beam computed tomography for heart, lung, colon, and total body scanning are new clinical areas where issues of radiation dosimetry have to be considered (13,14).

Currently, the FAA and airlines consider flight personnel (including flight attendants) as radiation workers. As such, they are allowed a regulatory dose limit 50 times the dose limit allowable to the general public. According to recent estimates, over 400,000 frequent fliers travel over 75,000 air miles each year, which means that they will exceed radiation dose limits to the general public from galactic (cosmic) radiation during flight (15). The radiation exposure during flight varies with altitude, flight time, air route, and solar flare activity. As an example, a routine flight form New York to Chicago (highest altitude 37,000 feet) yields a radiation dose rate of 0.0039 mSv per block hour. (The block hour begins when the aircraft leaves the blocks before takeoff and ends when it reaches the blocks after landing.) A flight from Athens, Greece to New York (highest altitude 41,000 feet) yields a radiation dose rate of 0.0063 mSv per block hour. The total radiation dose from the New York to Chicago route is 0.0089 mSv and the Athens t New York flight is 0.0615 mSv. For reference, the annual exposure limit for the general public is 1 mSv. The only remediation recommended by the FAA for radiation exposure during fight to is to limit flight and avoid traveling during periods of increased solar flare activity. Airline crew members flying long-haul high-altitude routes receives, on average, greater exposure each year than do radiation workers in ground-based industries where radioactive sources or radiation-producing machines are used (16).

The United States military is aware of and concerned about potential radiation exposures to out troops. Perhaps the most obvious population risk in the military is pilots flying long, high-altitude missions. The expected radiation doses would be in accordance with the estimates outlined above. The most recent U.S. Army study on the issue recognizes four nuclear radiation exposure risk categories of military personnel based on their likelihood and extent of exposure (17, Table 2). The army currently has three radiation protection programs to address these risk categories. One is applied to those individuals whose duties parallel those of civilian radiation workers. These include military personnel, such as x-ray technicians, radiologists who do radiological examinations, researchers who use radionuclides, and technicians who maintain radioactive commodities, such as radiation detection instruments and calibration sources. The second applies to soldiers whose primary occupation does not usually expose them to radiation. These are soldiers who might respond to a military situation, such as that covered by Allied Command Europe Directive (ACE) 80-63, in which radiation is present, but at doses not exceeding 700 mSv. The third category applies to those situations involving extremely high radiation exposure, such as nuclear war.

TABLE 2

Revised, Low-Level Radiation Guidance for Military Operations

| Total Cumulative Dose* | Radiation Exposure State Category | Recommended Actions | Increased Risk of Long Term Fatal Cancer** |
|---|---|---|---|
| <0.5 mGy | 0 | None | None |
| 0.5-5 mGy | 1A | Record individual dose readings Initiate periodic monitoring | 1:4,000 |
| 5-50 mGy | 1B | Record individual dose readings Continue monitoring Initiate rad survey Prioritize tasks Establish dose control measure as part of operations | 1:400 |
| 50-100 mGy | 1C | Record individual dose readings Continue monitoring Update survey Continue dose-control measures | 1:200 |

TABLE 2-continued

Revised, Low-Level Radiation Guidance for Military Operations

| Total Cumulative Dose* | Radiation Exposure State Category | Recommended Actions | Increased Risk of Long Term Fatal Cancer** |
|---|---|---|---|
| 100-250 mGy | 1D | Execute priority tasks only*<br>Record individual dose readings<br>Continue monitoring<br>Update survey<br>Continue dose control measures<br>Execute critical tasks only** | 1:80 |
| 250-700 mGy | 1E | Record individual dose readings<br>Continue monitoring<br>Update survey<br>Continue dose control measures<br>Execute critical tasks only | 1:30 |

*The use of the measurement millisievert is preferred in all cased. However, due to the fact that normally the military has only the capability to measure milligray (mGy), to the fact that normally the military has only the capability to measure milligray (mGy), as long as the ability to obtain measurement in millisievert is not possible, U.S. forces will use milligray. For whole body gamma irradiation, 1 mGy is equal to 1 mSv. All doses should be kept as low as reasonably achievable (ALARA). This will reduce the risk to individual soldiers and will retain maximum operational flexibility fur future employment of exposed soldiers.
**This is in addition to the 1:5 and 1:4 incidence of fatal cancer among the general population. Increased risk is given of induction of fatal cancer (losing an average) of 24 years of life for personnel ages 20-20 years). It must be noted that higher radiation dose rates produce proportionately more health risks than the same total dose given over a long period.
***Examples of priority tasks are those missions to avert danger to persons or to prevent damage from spreading.
****Examples of critial tasks are those missions required to save lives.

*The use of the measurement millisievert is preferred in all cased. However, due to the fact that normally the military has only the capability to measure milligray (mGy), as long as the ability to obtain measurement in millisievert is not possible, U.S. forces will use milligray. For whole body gamma irradiation, 1 mGy is equal to 1 mSv. All doses should be kept as low as reasonably achievable (ALARA). This will reduce the risk to individual soldiers and will retain maximum operational flexibility fur future employment of exposed soldiers.

**This is in addition to the 1:5 and 1:4 incidence of fatal cancer among the general population. Increased risk is given of induction of fatal cancer (losing an average of 24 years of life for personnel ages 20-30 years). It must be noted that higher radiation dose rates produce proportionately more health risks than the same total dose given over a longer period.

***Examples of priority tasks are those missions to avert danger to persons or to prevent damage from spreading.

****Examples of critical tasks are those missions required to save lives.

This study committee made four recommendations:

1) When making decisions, commanders should consider the long-term health effects that any action may have on their troops. This recommendation was extended such that it became standard operating policy.

2) The U.S. Department of Defense should develop and clearly express an underlying philosophy for radiation protection. Specifically, the committee suggested, a. application and adaptation of the system recommended by the International Commission of Radiological Protection, b. in peacetime or nonemergency situations, soldiers should be accorded the same level of protection accorded civilians, and c. in settings in which an intervention is required and specific numerical dose limits are neither applicable nor practical, commanders should justify the mission (there is more benefit than risk), examine competing risks, and optimize the mission (identify way to minimize dose without jeopardizing the mission).

3) Military personnel should receive appropriate training in both radiation effects and protection. Their training will need to vary on the basis of the particular level of potential exposure and the task at hand.

4) A program of measurement, recording, maintenance, and use of dosimetry and exposure information is essential.

The programs, once again, include no protection measures other than controlling time, distance, and physical shield.

Radiation workers experience a broad spectrum of working conditions that have radiation exposure as a normal part of the workplace environment. Examples include medical radiology workers, nuclear power plant workers, and worker who use radiation and radioactive materials in research. As mentioned above, commercial flight crews are also considered to be radiation workers. Owing to this occupational classification, radiation workers are allowed to receive 50 times the radiation dose allowed to the general public. Radiation workers also differ from the general public in that they receive training about the risks of radiation exposure and are monitored for their radiation exposure as part of their working paradigm. The nuclear regulatory commission (NRC) has established occupational dose limits as noted previously and procedures for monitoring and record-keeping. These standards and regulations rely solely on time, distance, and physical shielding as methods of radiation protection.

SUMMARY OF THE INVENTION

The present invention provides a formulation consisting essentially of:

| | |
|---|---|
| Vitamin A (palmitate) | 5,000 I.U. |
| Natural mixed carotenoids | 15 mg |
| Vitamin D-3 (cholecalciferol) | 400 I.U. |
| Natural soucre Vitamin E | |
| (d-alpha tocopherol) | 100 I.U. |
| (d-alpha tocopheryl acid succinate) | 100 I.U. |
| Buffered Vitamin C (calcium ascorbate) | 500 mg |
| Thiamine mononitrate | 4 mg |
| Riboflavin | 5 mg |
| Niacinamide ascorbate | 30 mg |
| d-calcium pantothenate | 10 mg |
| Pyridoxine hydrochloride | 5 mg |
| Cyanocobalamin | 10 µg |
| Folic Acid (Folacin) | 800 µg |
| D-Biotin | 200 µg |
| Selenium (1-seleno-methionine) | 100 µg |
| Chromium picolinate | 50 µg |
| Zinc glycinate | 15 mg |
| Calcium citrate | 250 mg |
| Magnesium citrate | 125 mg |

Plus a booster formulation selected from a group consisting essentially of 1000 mg of vitamin C, 400 international units of d-alpha tocopheryl acid succinate, 200 international units of alpha tocopherol, 500 mg of N-acetyl cysteine, 50 mg of natural mixed carotenoids, and 100 mg of alpha lipoic acid, wherein said formulation is designed to reduce the risk in humans exposed to ionizing radiation of becoming subjected to at least one condition selected from the group consisting essentially of radiation-induced acute leukemia, breast cancer, thyroid cancer and other somatic and heritable mutations.

In another embodiment, the dosage is taken prior to anticipated exposure. In yet another embodiment, the dosage is taken after exposure. In still another embodiment, the formulation is taken by user after exposure for a period of at least seven days.

In still yet another embodiment, the formulation is designed for a human who receives an effective dose of ionizing radiation of 0.5 mSv or less. In a further embodiment, the formulation is designed for a human who receives an effective dose of ionizing radiation of 0.5-5 mSv. In yet a further embodiment, the formulation is designed for a human who receives internal radionuclide exposures.

In still a further embodiment, the formulation consisting essentially of antioxidants, said antioxidants are selected from the group consisting essentially of vitamin C, vitamin E, N-acetyl cysteine, natural mixed carotenoids, and alpha-lipoic acid, vitamin A (palmitate), vitamin D-3 (cholecalciferol), thiamine mononitrate, riboflavin, niacinamide ascorbate, d-calcium pantothenate, pyridoxine hydrochloride, cyanocobalamin, folic acid, D-Biotin, selenium (1-seleno-methionine), chromium picolinate, zinc glycinate, calcium citrate and magnesium citrate and mixtures thereof; and plus a booster formulation selected from a group consisting essentially of vitamin C, d-alpha tocopheryl acid succinate, alpha tocopherol, N-acetyl cysteine, natural mixed carotenoids and alpha lipoic acid, said formulation is designed to reduce the risk in humans exposed to doses of ionizing radiation of becoming subjected to at least one condition selected from the group consisting essentially of radiation-induced acute leukemia, breast cancer, thyroid cancer and other somatic and heritable mutations.

In yet a further embodiment, the formulation comprises at least one glutathione elevating agent. In still a further embodiment, the dosage level of antioxidants is proportionate to the radiation level exposed to by a human. In still yet a further embodiment, the formulation is designed for a human who receives an effective dose of ionizing radiation of 0.5 mSv or less.

In another further embodiment, the antioxidants consist essentially of 250 mg of vitamin C, 200 international units of d-alpha acid succinate, and 250 mg of N-acetyl cysteine and the complete dosage is taken 1 hour prior to imaging study. In yet another embodiment, the formulation is designed for a human who receives an effective dose of ionizing radiation of 0.5-5 mSv In still another embodiment, the antioxidants consist essentially of 500 mg of buffered vitamin C, 400 international units of d-alpha tocopheryl acid succinate, 250 mg of N-acetyl cysteine, 15 mg of natural mixed carotenoids, and 30 mg of alpha-lipoic acid and a complete dosage is taken 1 hour prior to an imaging study.

In still yet another embodiment, the formulation is designed for a human who receives an effective dose of ionizing radiation of 5-15 mSv. In another embodiment, the antioxidants consist essentially of 500 mg of buffered vitamin C, 400 international units of d-alpha tocopheryl acid succinate, 250 mg of N-acetyl cysteine, 15 mg of natural mixed carotenoids, and 30 mg of alpha-lipoic acid and a complete dosage is taken 24 hours and 1 hour prior to an imaging study and 24 hours after the imaging study. In yet another embodiment, the formulation is designed for a human who receives an effective dose of ionizing radiation of 15-250 mSv.

In still another embodiment, the antioxidants consists essentially of 500 mg of buffered vitamin C, 400 international units of d-alpha tocopheryl acid succinate, 500 mg of N-acetyl cysteine, 30 mg of natural mixed carotenoids, and 60 mg of alpha lipoic acid and a complete dosage is taken 48 hours, 24 hours and 1 hour prior to imaging study and 24 hour after imaging study.

In yet another embodiment, the antioxidants consist essentially of:

| | |
|---|---|
| Vitamin A (palmitate) | 3,000 I.U.-10,000 IU |
| Natural mixed carotenoids | 10 mg-50 mg |
| Vitamin D-3 (cholecalciferol) | 400 I.U.-1000 IU |
| Natural soucre Vitamin E | |
| (d-alpha tocopherol) | 50 IU-400 I.U. |
| (d-alpha tocopheryl acid succinate) | 50 IU-400 I.U. |
| Buffered Vitamin C (calcium ascorbate) | 250 mg-2000 mg |
| Thiamine mononitrate | 2 mg-20 mg |
| Riboflavin | 3 mg-30 mg |
| Niacinamide ascorbate | 20 mg-60 mg |
| d-calcium pantothenate | 5 mg-50 mg |
| Pyridoxine hydrochloride | 5 mg-50 mg |
| Cyanocobalamin | 5 mcg-50 mcg |
| Folic Acid (Folacin) | 200 mcg-1600 mcg |
| D-Biotin | 50 mcg-400 mcg |
| Selenium (1-seleno-methionine) | 50 mcg-400 mcg |
| Chromium picolinate | 50 mcg-200 mcg |
| Zinc glycinate | 10 mg-30 mg |
| Calcium citrate | 100 mg-500 mg |
| Magnesium citrate | 50 mg-200 mg |

In still yet another embodiment, the booster formulation consist essentially of: 200-2000 mg of vitamin C, 100-800 international units of d-alpha tocopheryl acid succinate, 100-800 international units of alpha tocopherol, 100-500 mg of N-acetyl cysteine, 10-50 mg of natural mixed carotenoids, and 15-100 mg of alpha lipoic acid.

In a further embodiment, the present invention provides for a method of manufacturing a formulation, said method comprising admixing antioxidants, said antioxidants consist essentially of:

| | |
|---|---|
| Vitamin A (palmitate) | 3,000 I.U.-10,000 IU |
| Natural mixed carotenoids | 10 mg-50 mg |
| Vitamin D-3 (cholecalciferol) | 400 I.U.-1000 IU |
| Natural soucre Vitamin E | |
| (d-alpha tocopherol) | 50 IU-400 I.U. |
| (d-alpha tocopheryl acid succinate) | 50 IU-400 I.U. |
| Buffered Vitamin C (calcium ascorbate) | 250 mg-2000 mg |
| Thiamine mononitrate | 2 mg-20 mg |
| Riboflavin | 3 mg-30 mg |
| Niacinamide ascorbate | 20 mg-60 mg |
| d-calcium pantothenate | 5 mg-50 mg |
| Pyridoxine hydrochloride | 5 mg-50 mg |
| Cyanocobalamin | 5 mcg-50 mcg |
| Folic Acid (Folacin) | 200 mcg-1600 mcg |
| D-Biotin | 50 mcg-400 mcg |
| Selenium (1-seleno-methionine) | 50 mcg-400 mcg |
| Chromium picolinate | 50 mcg-200 mcg |
| Zinc glycinate | 10 mg-30 mg |
| Calcium citrate | 100 mg-500 mg |
| Magnesium citrate | 50 mg-200 mg |

In another further embodiment, the method further comprises preparing a booster formulation, said method comprises admixing said booster formulation consisting essentially of: 200-2000 mg of vitamin C, 100-800 international units of d-alpha tocopheryl acid succinate, 100-800 international units of alpha tocopherol, 100-500 mg of N-acetyl cysteine, 10-50 mg of natural mixed carotenoids, and 15-100 mg of alpha lipoic acid.

In yet another further embodiment, the formulation and the formulation booster are designed to reduce the risk in humans exposed to doses of ionizing radiation of becoming subjected to at least one condition selected from the group consisting essentially of radiation-induced acute leukemia, breast cancer, thyroid cancer and other somatic and heritable mutations.

In another embodiment, the booster formulation is first prepared being admixed with said formulation. In still another embodiment, the said formulation and the booster formulation are combined together and provided to the patient together. In yet another embodiment, the formulation and the booster formulation are prepared separately and provided to the patient separately.

In one further embodiment, the present invention provides for a micronutrient formulation, the formulation comprises: a first composition comprising alpha tocopherol and derivative esters of alpha tocopherol, the derivative esters of alpha tocopherol being selected from a group consisting essentially of alpha tocopheryl acetate, alpha tocopheryl palmitate, alpha tocopheryl succinate, alpha tocopheryl nicotinate and mixtures thereof; a second composition comprising vitamin A and natural-mixed carotenoids; and a third composition comprising calcium ascorbate. For purposes of this invention, natural-mixed carotenoids are defined as a natural extract of the algae species *Dunaliella salina*, the majority of which is beta carotene that contains various other natural carotenoids present in smaller amounts.

In a further embodiment, the method of the present invention wherein the percentage of each composition is as follows: the first composition is from about 1 to about 50% of the formulation; the second composition is from about 1 to about 50% of the formulation; and the third composition is from about 1 to about 50% of the formulation.

In another embodiment, the formulation further comprises a fourth composition, and the fourth composition is selected from a group consisting essentially of B-vitamins, selenium, zinc, magnesium, chromium and mixtures thereof. In yet another embodiment, the first, second, third and fourth compositions function as dietary micronutrients. For purposes of this invention, the term "dietary micronutrients" are defined as nutrients, including but not limited to vitamins and minerals that are consumed through the diet in small amounts and are distinct from dietary macronutrients which are defined as fats, proteins and carbohydrates. Dietary micronutrients include, but are not limited to tocopherols and tocopheryl esters (Vitamin E), Vitamin A, Vitamin C, Vitamin D, B-Vitamins, selenium, calcium, magnesium, zinc, carotenoids (e.g. beta carotene), and chromium.

In still another embodiment, the calcium ascorbate in the third composition is a source of vitamin C. In still yet another embodiment, the formulation further comprises a fifth composition, and the fifth composition is selected from a group consisting essentially of alpha lipoic acid, co-enzyme Q10, L-carnitine, n-acetyl cysteine and mixtures thereof. In a further embodiment, the fifth composition functions as an endogenous micronutrient. For purposes of this invention, the term "endogenous micronutrients" are defined as nutrients that are normally produced by the body. Due to factors such as aging, disease, physical activity level and environmental stressors, optimal amounts of these endogenous micronutrients may no longer be present in the body and need to be provided through supplementation. Endogenous micronutrients can be included in dietary supplements from synthetic or natural sources. Endogenous micronutrients include, but are not limited to lipoic acid, N-acetyl cysteine, nicotinamide adenine dinucleotide (NADH), l-carnitine, and coenzyme Q10.

In another further embodiment, the formulation further comprises reduced nicotinamide adenine dinucleotide.

In yet a further embodiment, the present invention provides for a micronutrient formulation system, the system comprises: a first composition comprising alpha tocopheryl and derivative esters of alpha tocopherol, the derivative esters of alpha tocopherol being selected from a group consisting essentially of alpha tocopheryl acetate, alpha tocopheryl palmitate, alpha tocopheryl succinate, alpha tocopheryl nicotinate and mixtures thereof; a second composition comprising vitamin A and natural-mixed carotenoids; a third composition comprising calcium ascorbate; a fourth composition selected from a group consisting essentially of B-vitamins, selenium, zinc, magnesium, chromium and mixtures thereof; and a fifth composition selected from a group consisting essentially of alpha lipoic acid, co-enzyme Q10, L-carnitine, n-acetyl cysteine and mixtures thereof, wherein said formulation is without iron, copper and manganese.

In still a further embodiment, the formulation system of the present invention wherein the first composition is from about 1 to about 50% of the formulation; the second composition is from about 1 to about 50% of the formulation; the third composition is from about 1 to about 50% of the formulation; the fourth composition is from about 1 to about 50% of the formulation; and the fifth composition is from about 1 to about 50% of the formulation.

In still yet a further embodiment, the formulation system of the present invention is consumed by the user at least twice per day.

In another further embodiment, the present invention provides for a method of manufacturing a micronutrient formulation comprising: admixing a first composition comprising alpha tocopheryl and derivative esters of alpha tocopherol, and the derivative esters of alpha tocopherol being selected from a group consisting essentially of alpha tocopheryl acetate, alpha tocopheryl palmitate, alpha tocopheryl succinate, alpha tocopheryl nicotinate and mixtures thereof; and then admixing a second composition comprising vitamin A and natural-mixed carotenoids; and then admixing a third composition comprising calcium ascorbate; and then admixing a fourth composition comprising selected from a group consisting essentially of B-vitamins, selenium, zinc, magnesium, chromium and mixtures thereof; and then admixing with a fifth composition selected from a group consisting essentially of alpha lipoic acid, co-enzyme Q10, L-carnitine, n-acetyl cysteine and mixtures thereof. In one embodiment, the individual compositions are first admixed or combined and then the first composition is admixed with the second and then the first and second compositions are then admixed with the third composition; then the first second and third mixed compositions are then admixed with the fourth composition and then the fifth composition is admixed at the end. In another embodiment, the compositions are all admixed together. In still another embodiment, the compositions can be added in any random order.

In a further embodiment, the method of the present invention wherein the percentage of each composition is as follows: the first composition is from about 1 to about 50% of the formulation; the second composition is from about 1 to about 50% of the formulation; the third composition is from about 1 to about 50% of the formulation; the fourth composition is from about 1 to about 50% of the formulation; and the fifth composition is from about 1 to about 50% of the formulation.

In a further embodiment, the method of the present invention wherein the percentage of each composition is as follows: the first composition is from about 1 to about 30% of the formulation; the second composition is from about 1 to about 30% of the formulation; the third composition is from about 1 to about 20% of the formulation; the fourth composition is from about 1 to about 20% of the formulation; and the fifth composition is from about 1 to about 20% of the formulation.

In another further embodiment, the method of the present invention further comprises admixing reduced nicotinamide adenine dinucleotide. In yet another embodiment, the formulation is consumed twice a day. In still yet another embodiment, the formulation is without iron, copper and manganese.

In a further embodiment, the formulation is designed to prevent excess production of free radical environment by the administration of said formulation to a patient.

In another further embodiment, the present invention relates to a micronutrient formulation comprises: a first composition comprising Vitamin A, Vitamin C, Vitamin E and natural mixed carotenoids; and a second composition comprising lipoic acid. In yet a further embodiment, the formulation further comprises a third composition, and the third composition is selected from a group consisting essentially of co-enzyme Q10, L-carnitine, n-acetyl cysteine and mixtures thereof. In still a further embodiment, the formulation is consumed by the user at least twice per day.

If it could be possible to devise a strategy to reduce the potential adverse effects of radiation exposure, it certainly seems reasonable that this approach should be undertaken regardless of how small the actual risk of injury might be. Federal law by regulatory code (C.F.R. 21 and C.F.R. 35) emphasizes ALARA guidelines as they relate to occupational radiation exposure. This concept should be extended to the biological consequences of the doses received by all classes of exposed individuals, including patients. The guidelines could be referred to as DALARA (damage as low as reasonably achievable), whereby both the dose and its harmful consequences could be minimized without interfering with the efficacy, ease, or cost of diagnostic procedures, or occupational and other activities. This novel concept, supported by extensive data, is based on reducing radiation-derived free radical damage by antioxidant supplementation. Special attention needs to be given to population groups under chronic risk situations like frequent fliers, radiation workers, flight crews, and military personnel in combat theatres of operation. In such cases, episodic dosing with antioxidants is not adequate to achieve ALARA principles. These population groups should achieve and maintain higher antioxidant loads than person with little or no expectation of radiation exposure.

In accordance with the present invention, twice daily dosing with a properly designed multiple antioxidant formulation is employed to maintain desired antioxidant loads in the body.

When chronically exposed (or chronic risk of exposure) individuals can be reasonably expected to incur an acute exposure, such as dangerous combat missions or any flight operations, they should supplement their regular antioxidant regimen with additional doses of selected antioxidants to protect against the anticipated exposure.

More particularly, the present invention is directed to a method for protecting humans in need of such protection from physical damage caused by ionizing radiation comprising administering to said humans on a defined basis prior to and after exposure to such radiation a plurality of antioxidants at a dosage level directly proportional to the radiation level likely to be encountered.

DETAILED DESCRIPTION OF THE INVENTION

As required, detailed embodiments of the present invention are disclosed herein; however, it is to be understood that the disclosed embodiments are merely exemplary of the invention that may be embodied in various forms. The examples disclosed herein are not to be interpreted as limiting, but merely as a basis for the claims and as a representative basis for teaching one skilled in the art to variously employ the present invention.

Although brief medical x-rays themselves may not cause detectable damage, serial imaging, future screening studies (the importance of which cannot be currently predicted), flight exposures, military operations exposures, occupational exposures, and other factors, such as diet, disease status, and environmental exposure, and the like may be clinically significant.

Relevant findings from basic scientific studies underscore this clinical concern. For example, a dose of 2 rem does not cause detectable mutations in normal human lymphocytes in culture. However, if the cells are irradiated with the same dose and treated with caffeine for a few hours after radiation exposure, an increased rate of cellular mutations is observed. This suggests that radiation-induced changes could be repaired in the normal course of events, but that subsequent exposure to caffeine impairs this normal cellular protective mechanism. In addition, a radiation dose that by itself would not be sufficient to induce cancer in an in vitro experimental system is able to do so in the presence of tumor promoters, such as phorbol ester, estrogen, and others. Furthermore, x-rays increase the incidence of cancer in cell culture by several folds when combined with chemical carcinogens, certain DNA viruses, ultraviolet radiation, or ozone exposure. Clearly, the potential hazard of even small radiation doses should not be ignored, since the target population readily interacts with agents present in the diet and environment, as well as other factors present in individual lifestyles.

Risk Categories

The following risk categories are general guidelines only and refer to acute exposures. The examples listed are not totally inclusive. The actual risk for any particular person may be modified by age and health status. The actual designation for all persons should be determined by healthcare or radiation physics professionals.

Population groups experiencing chronic radiation exposure risk, such as radiation workers (including commercial and military flight crews and field combat personnel), should maintain a higher baseline antioxidant load by taking a multiple antioxidant formulation (SEVAK) two times a day. They should then take the appropriate radioprotective formulation when the acute risk of exposure is expected (daily necessary). Categories 2-4 are equivalent with respect to formulation and can be regarded to be adequate for exposures less than 15 sMv effective dose when used for acute exposures only.

Category 1: Effective Dose 0.5 mSv or less

For example: chest x-ray, dental x-ray, abdominal x-ray, skeletal plain films, most commercial flight passengers.

Category 2: Effective Dose 0.5-5 mSv

For example: diagnose/screening computed tomography, urologic imaging, mammography, flight crews (commercial and military) and other radiation workers.

Category 3: Internal Radionuclide Exposures

For example: radionuclide imaging.

Category 4: Effective Dose 5-15 mSv

For example: limited diagnostic fluoroscopy (upper GI series, cholangiography, brain enema).

Category 5: Effective Dose Greater Than 15 mSv-250 mSv

For example: prolonged fluoroscopy/interventional radiology (coronary angiography, cerebral angiography, transluminal angioplasty) and some military personnel in combat operations (ground troops and seamen).

Category 6: Effective Dose 1000-2000 mSv

For example: radiation workers, civilian populations at risk near nuclear reactor sites in the event of an accident, and at risk military personnel in overseas theatres of operation.

Category 7: Effective Dose greater than 2000 mSv (not exceeding bone marrow syndrome doses)

For example: radiation workers, civilian populations at risk near nuclear sites in the event of an accident, and at risk military personnel in overseas theatres of operation.

Hereinafter, the term "imaging study" will be employed to include chest x-ray, dental x-ray, abdominal x-ray, skeletal plain films, diagnostic/screening computed tomography, urologic imaging, mammography, radionuclide imaging, limited diagnostic fluoroscopy, prolonged fluoroscopy/interventional radiology and the like.

The specific example below will enable the invention to be better understood. However, they are given merely by way of guidance and do not imply any limitation.

Example 1

Baseline Formulation (SEVAK)

| | |
|---|---|
| Vitamin A (palmitate) | 5,000 I.U. |
| Natural mixed carotenoids | 15 mg |
| Vitamin D-3 (cholecalciferol) | 400 I.U. |
| Natural source Vitamin E | |
| (d-alpha tocopherol) | 100 I.U. |
| (d-alpha tocopheryl acid succinate) | 100 I.U. |
| Buffered Vitamin C (calcium ascorbate) | 500 mg |
| Thiamine mononitrate | 4 mg |
| Riboflavin | 5 mg |
| Niacinamide ascorbate | 30 mg |
| d-calcium pantothenate | 10 mg |
| Pyridoxine hydrochloride | 5 mg |
| Cyanocobalamin | 10 µg |
| Folic acid (Folacin) | 800 µg |
| D-Biotin | 200 µg |
| Selenium (1-seleno methionie) | 100 µg |
| Chromium picolinate | 50 µg |
| Zinc glycinate | 15 mg |
| Calcium citrate | 250 mg |
| Magnesium citrate | 125 mg |

Radioprotective Formulations: (Boost Formulations)

Example 2

For Category 1 Personnel

| | |
|---|---|
| Vitamin C (calcium ascorbate) | 250 mg |
| Natural source vitamin E | 200 I.U. |
| (d-alpha tocopheryl acid succinate) | |
| N-acetyl cysteine | 250 mg |

Example 3

For Category 2 Personnel

| | |
|---|---|
| Vitamin C (calcium ascorbate) | 500 mg |
| Natural source vitamin E | 400 I.U. |
| (d-alpha tocopheryl acid succinate) | |
| N-acetyl cysteine | 250 mg |
| Natural mixed carotenoids | 15 mg |
| Alpha lipoic acid | 30 mg |

Complete dosage to be taken 1 hour prior to an imaging study or prior to each flight.

Example 4

For Category 3 Personnel

| | |
|---|---|
| Vitamin C (calcium ascorbate) | 500 mg |
| Natural source vitamin E | 400 I.U. |
| (d-alpha tocopheryl acid succinate) | |
| N-acetyl cysteine | 250 mg |
| Natural mixed carotenoids | 15 mg |
| Alpha lipoic acid | 30 mg |

Complete dosage to be taken 1 hour prior to an imaging study and 24 hours and 48 hours after the imaging study.

Example 5

For Category 4 Personnel

| | |
|---|---|
| Vitamin C (calcium ascorbate) | 500 mg |
| Natural source vitamin E | 400 I.U. |
| (d-alpha tocopheryl acid succinate) | |
| N-acetyl cysteine | 250 mg |
| Natural mixed carotenoids | 15 mg |
| Alpha lipoic acid | 30 mg |

Complete dosage to be taken 24 hours and 1 hour prior to an imaging study 24 hours after the imaging study.

Example 6

For Category 5 Personnel

| | |
|---|---|
| Vitamin C (calcium ascorbate) | 500 mg |
| Natural source vitamin E (d-alpha tocopheryl acid succinate) | 400 I.U. |
| N-acetyl cysteine | 500 mg |
| Natural mixed carotenoids | 30 mg |
| Alpha lipoic acid | 60 mg |

Complete dosage to be taken 48 hours, 24 hours and 1 hour prior to an imaging study 24 hours after the imaging study.

Example 7

For Category 6 Personnel

| | |
|---|---|
| Vitamin C (calcium ascorbate) | 1000 mg |
| d-alpha tocopheryl acid succinate | 400 I.U. |
| alpha tocopherol | 200 I.U. |
| N-acetyl cysteine | 500 mg |
| Natural mixed carotenoids | 40 mg |
| Alpha lipoic acid | 100 mg |

Complete dosage to be taken prior to anticipated exposure or as soon as possible after actual exposure. Continue complete dosage daily for seven days after exposure.

Example 8

For Category 7 Personnel

| | |
|---|---|
| Vitamin C (calcium ascorbate) | 2000 mg |
| d-alpha tocopheryl acid succinate | 600 I.U. |
| alpha tocopherol | 200 I.U. |
| N-acetyl cysteine | 1000 mg |
| Natural mixed carotenoids | 50 mg |
| Alpha lipoic acid | 150 mg |

Complete dosage to be taken prior to anticipated exposure or as soon as possible after actual exposure. Continue complete dosage daily for seven days after exposure.

It has been estimated that approximately 70-80% of the cellular damage induced by ionizing radiation is caused by free radicals. Therefore, it would be prudent to use agents that would quench these substances formed during x-ray exposure and protect the cells, organs, and total body from such injury.

Since World War II, extensive studies have been undertaken- to identify radioprotective compounds that have been shown to be effective when administered before exposure to irradiation. It is important to note that such compounds do not protect cells or organisms if they are administered after the ionizing radiation exposure. For modest radiation dose levels, the protective agents can be absorbed rapidly enough that they could be effective when given immediately before the exposure (within an hour or two). For enough levels of radiation dosage, it might be more desirable to achieve an established steady state of antioxidant concentration in the tissues initially, an then provide a booster dose of radioprotective agent immediately prior to exposure.

Research has determined that sulfhydryl (SH) compounds such as cysteamine, cystamine, and glutathione are among the most important and active intracellular antioxidants. Cysteamine protects animals against bone marrow and gastrointestinal radiation syndromes. The rationale for the importance of SH compounds is further supported by observations in mitotic cells. These are the most sensitive to radiation injury in terms of cell reproductive death and are noted to have the lowest level of SH compounds. Conversely, S-phase cells, which are the most resistant to radiation injury using the same criteria, have demonstrated the highest levels of inherent SH compounds. In addition, when mitotic cells were treated with cysteamine, they became very resistant to radiation. It has also been noted that cysteamine may directly protect cells against induced mutations. Unfortunately, cysteamine is extremely toxic when administered to human beings and, therefore, cannot itself be utilized in a radioprotective antioxidant regimen.

Thus, other SH compounds sharing the same antioxidant characteristics must be considered. Glutathione is a very effective antioxidant. However, when ingested by human beings it is completely hydrolyzed in the intestine and, therefore, can not be used as a radioprotective agent. However, N-acetylcysteine (NAC) and alpha lipoic acid actively increase the intracellular levels of glutathione without causing any toxicity. These rapidly absorbed compounds are tolerated by humans very well and would provide protection against ionizing radiation damage when given prior to the exposure. Indeed, these agents have also been shown to be of radioprotective value in experimental systems. Additional antioxidants such as vitamin E (d-alpha tocopheryl succinate), vitamin C (as calcium ascorbate) and the carotenoids (particularly natural beta-carotene) have been shown to be of marked radioprotective value in animals and in humans. A very recent report by the Armed Forces Radiobiology Research Institute showed good protection by vitamin E against lethal doses of cobalt-60 in mice.

The natural beta-carotene was selected because it most effectively reduces radiation-induced transformation in mammalian cells in culture. The d-alpha tocopheryl succinate form of vitamin E was selected because it is the most effective form of this micronutrient and also actively reduces the incidence of radiation-induced transformation in mammalian cells. This form of vitamin E is a more effective antioxidant than the more commonly utilized alpha tocopherol or other mixtures of tocopherols. Vitamin C as calcium ascorbate is beneficial because it is the most effective nonacidic form available for human use and, therefore, is less likely to cause stomach upset, diarrhea, and other problems that are observed in some individuals when taking therapeutic doses of vitamin C.

The most effective antioxidant approach to the free radical damage related to ionizing radiation-induced injury must utilize multiple micronutrients. It has been determined that multiple antioxidants are more effective than the individual agents themselves, and we propose this approach for several reasons. It is known that vitamin C and vitamin E are synergistic as antioxidants against free radicals because they are able to protect both the aqueous and lipid environments of the cells respectively. Indeed, one study has shown that oral intake of both vitamin C and vitamin E reduces the levels of fecal mutagens formed during digestion more than that produced by either of the individual antioxidants. It also must be recognized that oxygen level may vary widely within the tissues of whole organs or within the individual cells. This is especially true during the biologic insults that may occur with radiation-induced damage. It is known that beta-carotene acts more effectively as an antioxidant in high oxygen pressures, whereas vitamin E is a more effective antioxidant at reduced oxygen pressures.

Finally the body produces several types of free radicals (a myriad of oxygen-derived and nitrogen-derived species) during exposure to ionizing radiation. Clearly, each antioxidant has a different affinity for each specific class of free radicals. In a parallel manner, a combination of antioxidants is more effective in reducing the growth of tumor cells than the individual agents themselves. Therefore, to provide the most effective overall micronutrient approach to protect against radiation injury, a multiple component protocol utilized with a risk-based strategy seems essential and rational.

Most commercially available multiple supplement formulations contain iron, copper, and/or manganese. It is well known that these substances actively generate free radicals when combined with vitamin C. In addition, these minerals are more easily absorbed from the intestinal tract in the presence of antioxidants, such as vitamin C, and thereby increase the body stores of these minerals. Increased iron stores have been associated with many chronic human conditions, including heart disease, cancer and neurological diseases. Therefore, the addition of iron, copper or manganese to any multiple antioxidant preparation has no scientific merit for optimal health or disease prevention. Only in cases where a person has iron-deficiency anemia is a short-term iron supplement essential.

Many commercially available preparations contain heavy metals such as boron, vanadium, zirconium and molybdenum. Sufficient amounts of these metals are obtained from the diet and the daily consumption of excess amounts over long periods of time can be neurotoxic.

Many commercial preparations contain inositol, methionine and choline in varying amounts, e.g., 30 mg to 60 mg. These small doses serve no useful purpose for improving health because 400 mg to 1,000 mg of these nutrients are obtained daily from even the most minimal diet.

Para-aminobenzoic acid (PABA) is present in some multiple vitamin preparations. PABA has no biologic function in mammalian cells and can block the antibacterial effect of sulfonamides. Therefore, the effectiveness of a sulfonamide may be reduced in some patients being treated for bacterial infection.

Commercially sold multiple antioxidant preparations often contain varying amounts of N-acetyl cysteine or alpha lipoic acid. These nutrients are utilized because they are known to increase glutathione levels in cells. Reduced glutathione is a powerful antioxidant and actively protects both normal and cancer cells against radiation damage. Many cancer patients take antioxidant supplements without the knowledge of their oncologists. Therefore, the consumption of antioxidant preparations containing N-acetyl cysteine or alpha lipoic acid by these patients undergoing radiation therapy could interfere with important anti-cancer treatment.

The addition of both natural mixed carotenoids and vitamin A to any multiple vitamin preparation is essential, because beta-carotene not only acts as a precursor of vitamin A, but also performs important biological functions that cannot be performed by vitamin A. Beta-carotene increases the expression of the connexin gene, which codes for a gap junction protein that is necessary for maintaining the normal cellular phenotype. While other carotenoids, such as, lycopene, xanthophylls, and lutein are also important for health, they can be obtained from an adequate diet with tomato (lycopene), spinach (lutein), and paprika (xanthophylls) in amounts are higher than those that can be supplied from supplements. Therefore, the addition of a few milligrams of lycopene, xanthophylls, and lutein to any multiple vitamin preparation serves no useful purpose for health or disease prevention.

The proper ratio of two forms of vitamin E, d-alpha tocopherol, which is normally present in the body, and d-alpha succinate, to a multiple antioxidant preparation is essential. Alpha tocopheryl succinate is the most effective form of vitamin E inside the cells, where as alpha tocopherol can readily act as an antioxidant in the intestinal tract and in the extracellular environment of the body. Alpha-tocopherol at doses of 20-60 µg/ml can stimulate the immune system, while the beta, gamma, and delta forms at similar doses can inhibit the immune system. This effect of these forms of tocopherol may not be related to their antioxidant action and, since they are less effective than alpha tocopherol, their supplementation is not recommended.

Tocotrienols are also antioxidants, but they may inhibit cholesterol synthesis. Since this activity is not beneficial in healthy individuals, prolonged consumption of tocotrienols as a supplement is not optimal.

Vitamin C is usually administered as ascorbic acid, which can cause stomach upset, diarrhea and other complications in some individuals. However, using the calcium ascorbate form is most suitable because it is non-acidic and has not been shown to produce negative side effects. The use of potassium ascorbate and magnesium ascorbate in any vitamin preparation is unnecessary. Also, any multiple micronutrient preparation should include adequate amounts of B-vitamins (2-3 times of RDA) and appropriate minerals.

The risk of chronic illness may depend upon the relative consumption of protective versus toxic substances. If the daily intake of protective substances is higher than toxic agents, the incidence of chronic illness may be reduced. Since we know very little about the relative levels of toxic and protective substances in any diet, a daily supplement of micronutrients including antioxidants would assure a higher level of preventive protection.

The present invention also provides for the following formulation examples:

Example 9

Bioshield—R1 in Two Capsules

| | |
|---|---|
| Vitamin C (calcium ascorbate) | 500 mg |
| d-alpha tocopheryl succinate | 400 IU |
| Natural mixed carotenoids | 15 mg |
| Selenomethionine | 100 mcg |
| n-acetylcysteine | 250 mg |
| Alpha-lipoic acid | 30 mg |

Example 10

Bioshield—R2 in Four Capsules Daily

| | |
|---|---|
| Vitamin A (as palmitate) | 5,000 |
| Vitamin C (as calcium ascorbate) | 1,000 mg |
| Vitamin E (as d-alpha-tocpheryl succinate) | 200 IU |
| (as d-alpha-tocopherol) | 200 IU |
| Vitamin D (as cholocalciferol) | 400 IU |
| Vitamin B-1 (thiamine mononitrate) | 4 mg |
| Vitamin B-2 (riboflavin) | 5 mg |

| | |
|---|---|
| Niacin (as niacinamide ascorbate) | 30 mg |
| Vitamin B-6 (as pyrodioxine HCl) | 5 mg |
| Folate (Folic acid) | 800 mcg |
| Vitamin B-12 (as cyanocbalamin) | 10 mg |
| Biotin | 200 mcg |
| Pantothenic acid (as d-calcium pantothenate) | 10 mg |
| Calcium citrate | 250 mg |
| Magnesium citrate | 125 mg |
| Zinc (as zinc glycinate) | 15 mg |
| Selenium (as selenomethionine) | 200 mcg |
| Chromium (as chromium picolinate) | 50 mcg |
| Coenzyme Q10 | 30 mg |
| N-acetylcysteine | 250 mg |
| Alpha-lipoic acid | 30 mg |
| Natural mixed carotenoids | 15 mg |

Example 11

Bioshield—R3 in Six Capsules/Daily

| | |
|---|---|
| Vitamin A (as palmitate) | 5,000 |
| Vitamin C (as calcium ascorbate) | 1,000 mg |
| Vitamin E (as d-alpha-tocpheryl succinate) | 400 IU |
| (as d-alpha-tocopherol) | 200 IU |
| Vitamin D (as cholocalciferol) | 400 IU |
| Vitamin B-1 (thiamine mononitrate) | 4 mg |
| Vitamin B-2 (riboflavin) | 5 mg |
| Niacin (as niacinamide ascorbate) | 30 mg |
| Vitamin B-6 (as pyrodioxine HCl) | 5 mg |
| Folate (Folic acid) | 800 mcg |
| Vitamin B-12 (as cyanocbalamin) | 10 mg |
| Biotin | 200 mcg |
| Pantothenic acid (as d-calcium pantothenate) | 10 mg |
| Calcium citrate | 250 mg |
| Magnesium citrate | 125 mg |
| Zinc (as zinc glycinate) | 15 mg |
| Selenium (as selenomethionine) | 200 mcg |
| Chromium (as chromium picolinate) | 50 mcg |
| Coenzyme Q10 | 30 mg |
| N-acetylcysteine | 500 mg |
| Alpha-lipoic acid | 90 mg |
| Natural mixed carotenoids | 60 mg |

Numerous modifications and variations of the present invention are possible in light of the above teachings. It is therefore to be understood that within the scope of the attendant claims attached hereto, this invention may be practiced otherwise than as specifically disclosed herein.

What is claimed is:

1. A formulation consisting of antioxidants and a booster formulation, said antioxidants consisting of vitamin C, vitamin E, N-acetyl cysteine, natural mixed carotenoids, alpha-lipoic acid, vitamin A, vitamin D, thiamine mononitrate, riboflavin, niacinamide ascorbate, d-calcium pantothenate, pyridoxine hydrochloride, cyanocobalamin, folic acid, D-Biotin, selenium, chromium picolinate, zinc glycinate, calcium citrate, and magnesium citrate; and said booster formulation consisting of vitamin C, d-alpha tocopheryl acid succinate, alpha tocopherol, N-acetyl cysteine, natural mixed carotenoids and alpha lipoic acid, and wherein said formulation is designed to reduce the risk in humans exposed to doses of ionizing radiation of becoming subjected to at least one condition selected from the group consisting of radiation-induced acute leukemia, breast cancer, thyroid cancer and other somatic and heritable mutations caused by radiation exposure.

2. The formulation of claim 1 wherein a dosage level of the antioxidants is proportionate to a radiation level exposed to by the human.

3. The formulation of claim 1 wherein said formulation is designed for a human who receives an effective dose of ionizing radiation of 0.5 mSv or less.

4. The formulation of claim 1 wherein said formulation is designed for a human who receives an effective dose of ionizing radiation of 0.5-5 mSv.

5. The formulation of claim 4 wherein said booster formulation consists of 500 mg of vitamin C, 400 international units of d-alpha tocopheryl acid succinate, 250 mg of N-acetyl cysteine, 15 mg of natural mixed carotenoids, and 30 mg of alpha-lipoic acid and wherein the booster formulation is taken 1 hour prior to an imaging study.

6. The formulation of claim 1 wherein said formulation is designed for a human who receives an effective dose of ionizing radiation of 5-15 mSv.

7. The formulation of claim 6 wherein said booster formulation consists of 500 mg of vitamin C, 400 international units of d-alpha tocopheryl acid succinate, 250 mg of N-acetyl cysteine, 15 mg of natural mixed carotenoids, and 30 mg of alpha-lipoic acid and wherein the booster formulation is taken 24 hours and 1hour prior to an imaging study and 24 hours after the imaging study.

8. The formulation of claim 1 wherein said formulation is designed for a human who receives an effective dose of ionizing radiation of 15-250 mSv.

9. The formulation of claim 8 wherein said booster formulation consists of 500 mg of vitamin C, 400 international units of d-alpha tocopheryl acid succinate, 500 mg of N-acetyl cysteine, 30 mg of natural mixed carotenoids, and 60 mg of alpha lipoic acid and wherein the booster formulation is taken 48 hours, 24 hours and 1 hour prior to an imaging study and 24 hours after the imaging study.

10. A method of manufacturing a formulation of claim 1, said method comprising admixing the antioxidants and separately admixing the booster formulation.

11. The method of claim 10 wherein a dosage level of the antioxidants is proportionate to a radiation level exposed to by the human.

* * * * *